(12) United States Patent
Fan et al.

(10) Patent No.: US 11,744,448 B2
(45) Date of Patent: Sep. 5, 2023

(54) APPARATUS AND METHOD FOR INCREASING HEAT DISSIPATION CAPACITY OF A MEDICAL INSTRUMENT

(71) Applicant: INTUITIVE SURGICAL OPERATIONS, INC., Sunnyvale, CA (US)

(72) Inventors: Anqi Fan, Sunnyvale, CA (US); Tiejun Hu, Fremont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 499 days.

(21) Appl. No.: 16/611,002

(22) PCT Filed: May 8, 2018

(86) PCT No.: PCT/US2018/031670
§ 371 (c)(1),
(2) Date: Nov. 5, 2019

(87) PCT Pub. No.: WO2018/208834
PCT Pub. Date: Nov. 15, 2018

(65) Prior Publication Data
US 2020/0077879 A1    Mar. 12, 2020

Related U.S. Application Data

(60) Provisional application No. 62/503,521, filed on May 9, 2017.

(51) Int. Cl.
*A61B 1/12* (2006.01)
*A61B 1/00* (2006.01)

(52) U.S. Cl.
CPC .......... *A61B 1/128* (2013.01); *A61B 1/00066* (2013.01); *A61B 1/00071* (2013.01); *A61B 1/00131* (2013.01)

(58) Field of Classification Search
CPC .. A61B 1/128; A61B 1/00066; A61B 1/00071
See application file for complete search history.

(56) References Cited

U.S. PATENT DOCUMENTS

2006/0173344 A1    8/2006  Marian et al.
2007/0191684 A1*   8/2007  Hirata .................. A61B 1/0607
                                                    600/152
(Continued)

FOREIGN PATENT DOCUMENTS

CN    1794944 A     6/2006
CN    101392873 A   3/2009
(Continued)

OTHER PUBLICATIONS

International Search Report and Written Opinion for Application No. PCT/US2018/031670, dated Nov. 13, 2018, 19 pages.
(Continued)

*Primary Examiner* — Aaron B Fairchild
(74) *Attorney, Agent, or Firm* — HAYNES AND BOONE, LLP

(57) ABSTRACT

A method and apparatus for improving a heat dissipation capacity. An apparatus comprises an elongate member, a housing, and a heat pump device. The elongate member has a distal end and a proximal end. The housing is coupled to the proximal end of the elongate member. The heat pump device is disposed between the proximal end of the elongate member and the housing. The heat pump device is disposed at least partially outside the housing and is configured to transfer thermal energy between the elongate member and the housing. The heat pump device has a maximum outer diameter that is greater than a maximum outer diameter of the elongate member.

20 Claims, 3 Drawing Sheets

(56) References Cited

U.S. PATENT DOCUMENTS

| | | | |
|---|---|---|---|
| 2008/0228035 A1 | 9/2008 | Hagihara et al. | |
| 2009/0030278 A1* | 1/2009 | Minakuchi | A61B 1/00034 600/118 |
| 2010/0033559 A1* | 2/2010 | Yasunaga | A61B 1/051 348/E7.085 |
| 2010/0265733 A1 | 10/2010 | O'Leary et al. | |
| 2011/0306834 A1 | 12/2011 | Schrader et al. | |
| 2012/0095536 A1 | 4/2012 | Machold et al. | |
| 2014/0200406 A1 | 7/2014 | Bennett et al. | |
| 2014/0206939 A1* | 7/2014 | Eisele | A61B 1/128 600/156 |
| 2014/0221743 A1 | 8/2014 | Sugiyama et al. | |
| 2016/0242635 A1* | 8/2016 | Inoue | A61B 1/0684 |

FOREIGN PATENT DOCUMENTS

| CN | 101810462 A | 8/2010 |
|---|---|---|
| CN | 201840456 U | 5/2011 |
| CN | 103124514 A | 5/2013 |
| CN | 204765541 U | 11/2015 |
| CN | 105520708 A | 4/2016 |
| CN | 105916429 A | 8/2016 |
| JP | H10178571 A | 6/1998 |
| JP | H11299775 A | 11/1999 |
| JP | 2006198413 A | 8/2006 |
| JP | 2009254571 A | 11/2009 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2018/031670, dated Nov. 12, 2019, 12 pages.

DESHENG Xu et al., "Semiconductor Refrigeration and Application Technology," Shanghai Jiaotong University Press, 1999, pp. 113-114.

* cited by examiner

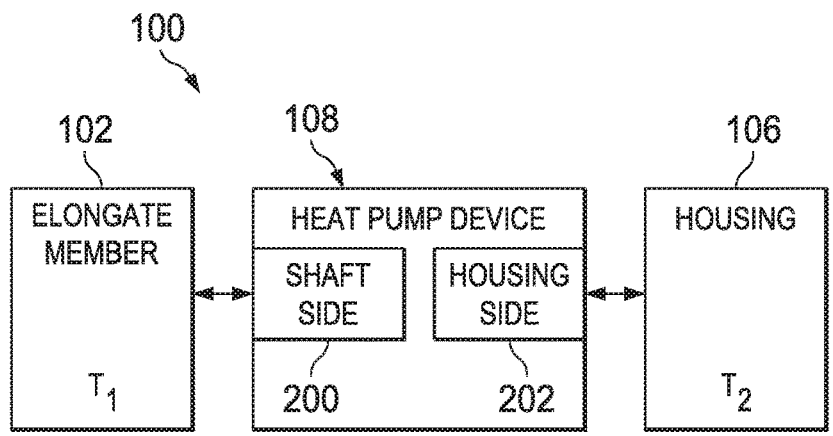
Fig. 2
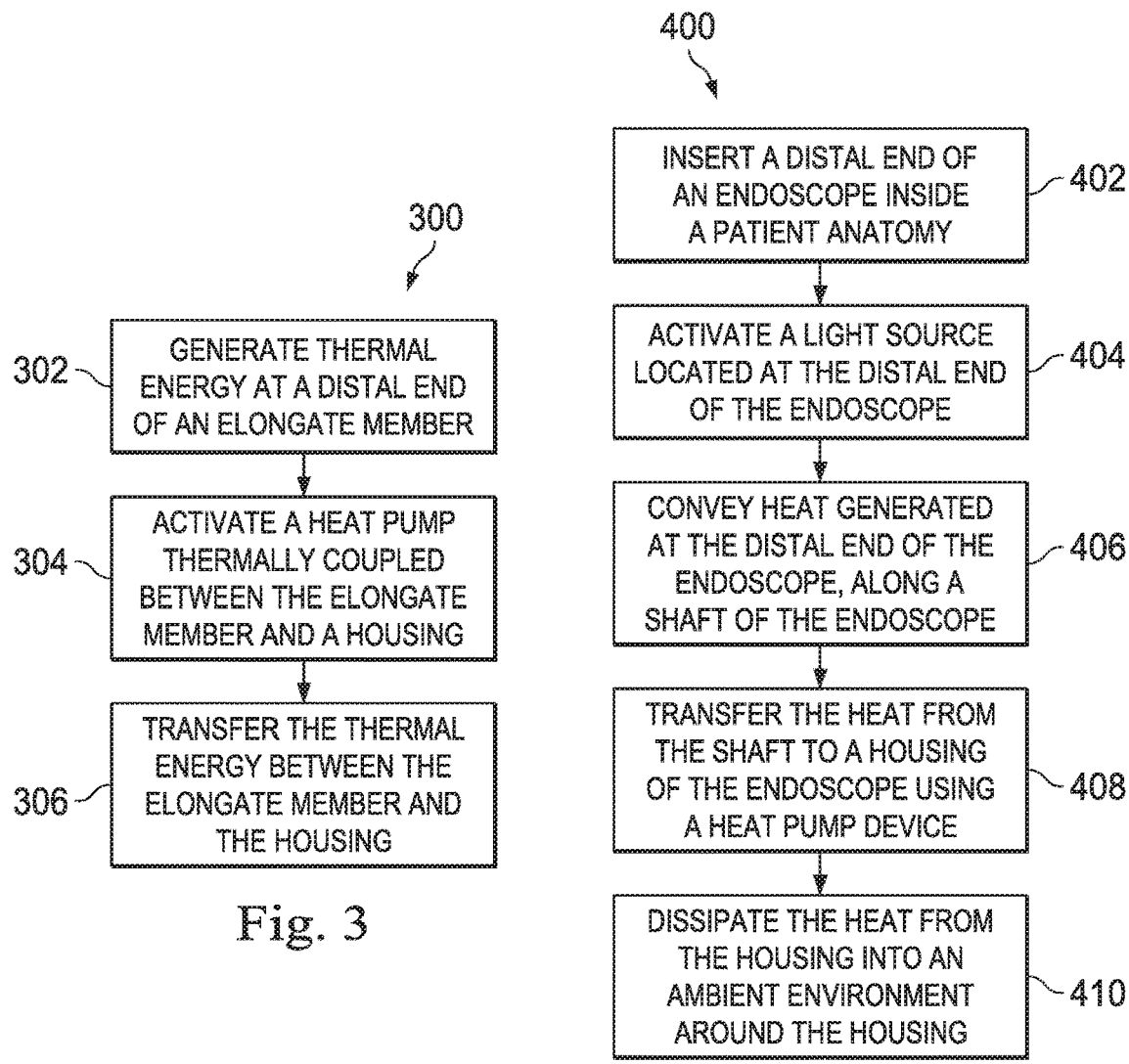
Fig. 3
Fig. 4

APPARATUS AND METHOD FOR INCREASING HEAT DISSIPATION CAPACITY OF A MEDICAL INSTRUMENT

CROSS-REFERENCE TO RELATED APPLICATIONS

This patent application is a U.S. national phase of International Application No. PCT/US2018/031670, filed May 8, 2018, which designated the U.S. and claims priority to and the benefit of the filing date of U.S. Provisional Application No. 62/503,521, filed May 9, 2017, which are incorporated by reference in their entirety.

FIELD

The present disclosure is directed to medical instruments and, in particular, medical instruments that generate heat. More particularly, the present disclosure is directed to systems and methods for increasing the heat dissipation capacity along a medical instrument, such as an endoscope.

BACKGROUND

Minimally invasive imaging instruments may be used for visual inspection of hard-to-reach or compact spaces within a patient's anatomy. An endoscope is an example of a minimally invasive imaging instrument that may include a shaft having a distal tip that can be inserted into the patient's body. A housing may be connected to the other end of the shaft. The housing may contain, for example, various optical components and electronic components that allow a human operator to view and/or record images captured at the distal tip of the shaft. The endoscope may provide illumination to the inspected anatomic area.

It may be desirable to improve image quality and power efficiency of the imaging instrument by locating some of the optical and electronic components near the distal tip of the shaft. With existing systems, such improvements have been limited by the need to maintain a distal tip anatomic contact temperature that is below a maximum contact temperature typically set by safety regulations. The maximum contact temperature may be, for example, the highest temperature at which the distal tip can safely come into direct contact with or within a selected range of an internal body part or patient tissue. Thus, improved systems and methods for maintaining the distal tip at a temperature equal to or below the maximum contact temperature may be desired.

SUMMARY

The embodiments of the invention are summarized by the claims that follow below.

In one illustrative embodiment, an apparatus comprises an elongate member, a housing, and a heat pump device. The elongate member has a distal end and a proximal end. The housing is coupled to the proximal end of the elongate member. The heat pump device is coupled between the elongate member and the housing. The heat pump device is configured to transfer thermal energy between the elongate member and the housing.

In another illustrative embodiment, an apparatus comprises an elongate member, a housing, and a heat pump device. The elongate member has a distal end and a proximal end. The housing is coupled to the proximal end of the elongate member. The heat pump device is coupled to at least one of the elongate member and the housing. The heat pump device is configured to change a first heat dissipation capacity of the elongate member and to change a second heat dissipation capacity of the housing.

In yet another illustrative embodiment, an apparatus comprises an elongate member, a housing, and a plurality of heat pump devices. The elongate member has a distal end and a proximal end. The housing is located near the proximal end of the elongate member. Each of the plurality of heat pump devices is located at a respective one of a plurality of positions along a heat path formed between the distal end of the elongate member and the housing. The plurality of heat pump devices transfers thermal energy to change a first heat dissipation capacity of the elongate member and to change a second heat dissipation capacity of the housing.

In still yet another illustrative embodiment, a method is provided. Thermal energy is generated at a distal end of an elongate member. The thermal energy is transferred between the elongate member and a housing coupled to a proximal end of the elongate member by activating a heat pump device thermally coupled between the elongate member and the housing.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 2 is an illustration of a schematic view of an imaging system in accordance with an illustrative embodiment;

FIG. 3 is an illustration of a method for improving heat dissipation capacity in accordance with an illustrative embodiment;

FIG. 4 is an illustration of a method for improving heat dissipation capacity in accordance with an illustrative embodiment.

DETAILED DESCRIPTION

Figure 1:
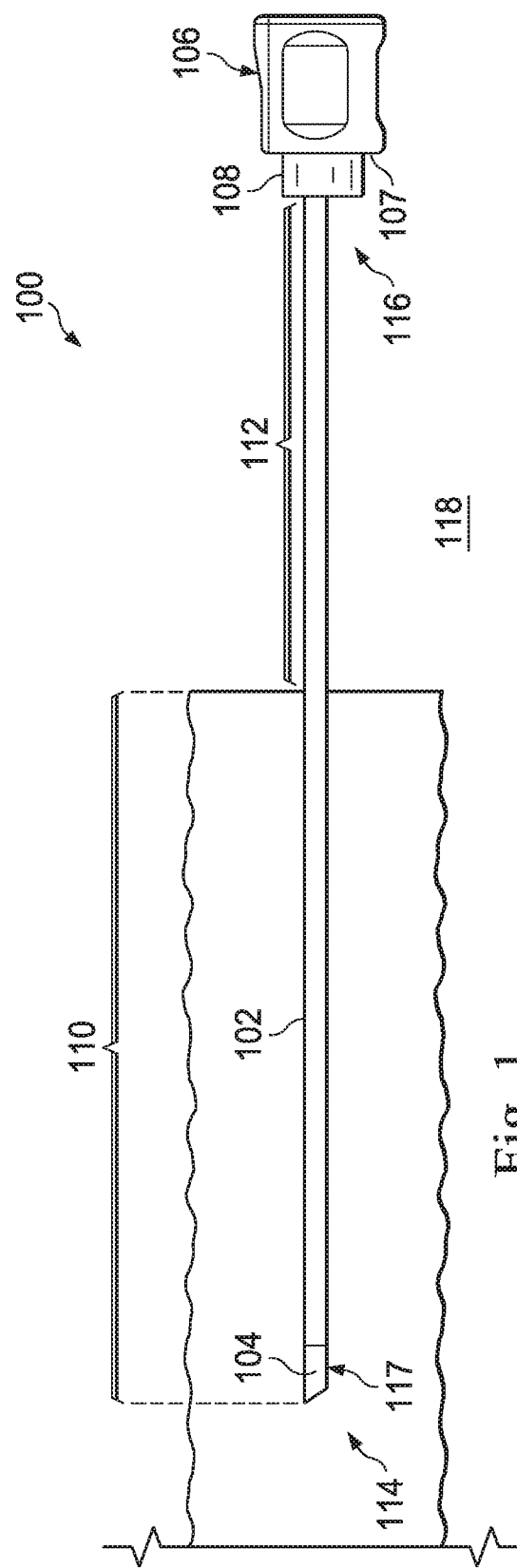
FIG. 1 is an illustration of an imaging system in accordance with an illustrative embodiment.

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances well known methods, procedures, components, and circuits have not been described in detail so as not to unnecessarily obscure aspects of the embodiments.

The illustrative embodiments recognize and take into account that it may be desirable to have an apparatus and method for dissipating the heat generated by the operation of components at the distal end of a medical instrument, such as an endoscope. The heat may be transferred from the distal end to a housing that is located outside of a patient's body. The heat may then be sunk into the ambient environment around the housing. The illustrative embodiments recognize that various factors may limit the heat dissipation capacity at the distal end of the endoscope. These factors may include, for example, without limitation, the maximum contact temperature of the distal tip, the ambient temperature of the ambient environment, and the thermal resistances of the electrical and mechanical parts located between the distal tip and the housing. Thus, the illustrative embodiments provide an apparatus and method for increasing the tip heat dissipation capacity and the housing heat dissipation capacity in the context of these limiting factors.

The illustrative embodiments described below provide a method and apparatus for increasing the heat dissipation capacity at various areas of interest along a medical imaging instrument, such as an endoscope. In one illustrative embodiment, an apparatus comprises an elongate member, a housing, and a heat pump device. The elongate member has a distal end and a proximal end. The housing is coupled to the proximal end of the elongate member. The heat pump device is coupled between the elongate member and the housing. The heat pump device is configured to transfer thermal energy between the elongate member and the housing. This transfer of thermal energy may include the heat dissipation capacities of the distal end and the housing. In particular, using the heat pump device may allow the heat from the distal end to be dissipated through the housing without needing to change the ambient temperature and without adding an undesired amount of weight or bulk to the endoscope.

Further, increasing the heat dissipation capacities at the distal end and housing may allow components that generate heat to be used at or near the tip without a temperature at the distal end exceeding the maximum contact temperature. For example, one or more illumination components, one or more electronic components, or a combination thereof may be relocated at or near a tip at the distal of the endoscope to improve the image quality, power efficiency, and robustness of the endoscope. In particular, moving these components towards the tip may help simplify the optics, thereby reducing the overall weight of the endoscope.

Referring to FIG. 1 of the drawings, an imaging system 100 is depicted in accordance with an illustrative embodiment. The imaging system 100 may be an instrument that can be used to visually and medically inspect various internal body parts and cavities inside a patient's anatomy. For example, the imaging system 100 may take the form of an endoscope used to provide views of the internal parts of a patient's anatomy.

In one illustrative embodiment, the imaging system 100 includes an elongate member 102, a housing 106, and a heat pump device 108. Depending on the implementation, the elongate member 102 may be rigid, flexible, articulated, partially flexible, or a combination thereof. Further, the elongate member 102 may be comprised of metal, plastic, a combination of the two, or some other suitable material. As one illustrative example, the elongate member 102 may take the form of a shaft having one or more internal passageways. The elongate member 102 may have a thermal resistance selected to help improve heat dissipation.

During a medical procedure in which the imaging system 100 is used to visualize an internal patient anatomy, a portion of the elongate member 102 may be inserted inside the patient's anatomy, while another portion of the elongate member 102 may be kept outside of the patient's anatomy. For example, without limitation, a first portion 110 of the elongate member 102 may be located inside the patient's anatomy, while a second portion 112 may be located outside the patient's anatomy.

The elongate member 102 has a distal end 114 and a proximal end 116. A distal tip 104 of the shaft is located at the distal end 114. In one illustrative embodiment, the tip 104 may be an integral part of the elongate member 102. In other illustrative embodiments, the tip 104 may be a separate part that is coupled to the elongate member 102.

The housing 106 is located near the proximal end 116 of the elongate member 102. In this illustrative embodiment, the housing 106 may be indirectly coupled to the proximal end 116 of the elongate member 102 via the heat pump device 108. The housing 106 may contain any number of different components. For example, without limitation, the housing 106 may contain one or more optical elements that allow a human operator to view images captured at the distal end 114 of the imaging system 100. These optical components may include, for example, without limitation, one or more mirrors, one or more lenses, one or more other optical components, or a combination thereof. Depending on the implementation, the housing 106 may contain additional components.

Further, the housing 106 may be comprised of one or more materials selected to improve heat dissipation. In one illustrative embodiment, the housing 106 is comprised of aluminum.

The imaging system 100 also includes a component 117 located at the distal end 114. The component 117 may generate thermal energy that causes the temperature of the distal end 114 to increase. In some illustrative embodiments, the component 117 takes the form of a light emitting diode (LED) or another type of powered light source or illumination source that generates thermal energy. In other illustrative embodiments, the component 117 may be a powered electronic component, such as a sensor or a signal transmitter, which generates thermal energy. In alternative embodiments where the thermal energy generating component 117 is omitted, the heat dissipation systems described herein may also be used to dissipate body heat or otherwise cool the distal end 114.

The distal end 114, and therefore the tip 104, has a maximum contact temperature ($T_C$) that is considered safe for when the distal end 114 comes into direct contact with or within a selected range of an internal body part or patient tissue. In one illustrative example, this selected range may be between about 2 millimeters and about 10 millimeters. The maximum contact temperature for the distal end 114 may be regulated by safety standards. As one illustrative example, the maximum contact temperature may be a value between about 40 degrees Celsius and 45 degrees Celsius. In other illustrative examples, the maximum contact temperature may be a value between about 40 degrees Celsius and about 50 degrees Celsius. Accordingly, the temperature of the distal end 114 may need to be controlled to ensure that the distal end 114 does not reach a temperature above the maximum contact temperature.

In this embodiment, the temperature of the distal end 114 may be controlled by dissipating the thermal energy generated by the component 117 along a main heat path from the tip 104 and into an ambient environment 118 around the housing 106. As one illustrative example, the heat may be transferred from the tip 104 at the distal end 114, along the elongate member 102, then spread to the housing 106, and finally dissipated from the housing 106 into the ambient environment 118.

The ambient environment 118 may have an ambient temperature ($T_A$). In some instances, the ambient temperature may be variable. For example, without limitation, the ambient environment 118 may be an operating room in a hospital or clinic. In some instances, the operating room may be maintained at a temperature selected between about 18 degrees Celsius and 23 degrees Celsius. Depending on the type of ambient environment 118, the ambient temperature may be maintained at a value between about 18 degrees Celsius and about 28 degrees Celsius.

The main heat path has an overall system temperature difference ($\Delta T_O$) that is bounded by the maximum contact temperature ($T_C$) for the distal end 114 and the ambient temperature ($T_A$) of the ambient environment 118. For example, when the maximum contact temperature is between about 40 degrees Celsius and 45 degrees Celsius and the ambient temperature is between about 23 degrees Celsius and 26 degrees Celsius, the overall system temperature difference may be between about 16 degrees Celsius and 20 degrees Celsius.

The heat pump device 108 accelerates the transfer of heat along the main heat path. In this embodiment, the heat pump device 108 is positioned between the elongate member 102 and the housing 106. More specifically, the heat pump device 108 may be coupled to the proximal end 116 of the elongate member 102 at one side of the heat pump device 108 and coupled to a distal side 107 of the housing 106 at an opposite side of the heat pump device 108. In this manner, the elongate member 102 may be indirectly coupled to the housing 106 through the heat pump device 108.

The heat pump device 108 is used to increase a heat dissipation capacity of the elongated member 102 and a heat dissipation capacity of the housing 106. In particular, the heat pump device 108 may increase the heat dissipation capacity of the elongated member 102 and the heat dissipation capacity of the housing 106 to accelerate overall heat dissipation along the main heat path and accelerate removal of heat from the distal end 114. The heat dissipation capacity of the elongate member may also be referred to as a tip heat dissipation capacity, a distal end heat dissipation capacity, or an elongate member heat dissipation capacity. The heat dissipation capacity of the housing may also be referred to as a housing heat dissipation capacity.

FIG. 2 is a schematic view of the imaging system 100. In this illustrative embodiment, the heat pump device 108 takes the form of a thermoelectric cooler. But in other illustrative embodiments, other types of devices that transfer thermal energy (i.e., heat) from a source of heat to a heat sink may be used.

As depicted, the heat pump device 108 has a shaft side 200 and a housing side 202. In this illustrative embodiment, the shaft side 200 is thermally coupled to the elongate member 102 and the housing side 202 is thermally coupled to the housing 106. The heat pump device 108 allows a temperature ($T_1$) of the proximal end 116 of the elongate member 102 to be controlled at a level lower than the ambient temperature of the ambient environment 118. Further, the heat pump device 108 allows a temperature ($T_2$) of the distal side 107 of the housing 106 to be controlled at a level higher than the maximum contact temperature for the distal end 114.

For example, when the ambient temperature is set to about 25 degrees Celsius, the temperature $T_1$ of the elongate member may be maintained at about 20 degrees Celsius with the operation of the heat pump device 108. Further, the heat pump device 108 controls the temperature $T_2$ of the distal side 107 housing 106 at substantially a value that is higher than the maximum contact temperature for the distal end 114. For example, without limitation, when the maximum contact temperature is set to about 42 degrees Celsius, the resulting temperature $T_2$ may be about 50 degrees Celsius. In this manner, the difference between the temperature $T_2$ and temperature $T_1$, which may be about 30 degrees Celsius, is greater than the overall system temperature difference ($T_C - T_A$) of about 17 degrees Celsius.

Accordingly, the proximal end 116 of the elongate member 102 may have a temperature, controlled by the heat pump device 108, lower than the temperature of the housing 106. Further, the shaft side 200 of the heat pump device 108 may have a temperature lower than the housing side 202 of the heat pump device 108. The heat pump device 108 allows heat to be transferred from the cooler elongate member 102 at the shaft side 200 to the warmer housing 106 at the housing side 202. Thus, the heat pump device 108 accelerates the heat transfer between the elongate member 102 and the housing 106.

In one illustrative embodiment, external power supplied to operate of the heat pump device 108 generates waste heat. The heat pump device 108 may also be capable of dissipating this waste heat through the housing 106. When the difference between the heat dissipation capacity of the housing 106 and the heat dissipation capacity of the elongate member 102 is greater than the rate at which the waste heat is generated, the housing 106 may be capable of dissipating the heat from both the elongate member 102 and the heat pump device 108. In one example, the heat dissipation capacity of the housing 106 achieved using the heat pump device may be about 7 Watts. The heat dissipation capacity of the elongate member 102 achieved using the heat pump device 108 may be about 3 Watts. If the rate at which the waste heat is generated by the heat pump device 108 is less than about 4 Watts, then the housing 106 may effectively dissipate the heat from both the distal end 114 and the heat pump device 108.

The illustrations in FIGS. 1 and 2 are not meant to imply physical or architectural limitations to the manner in which the different illustrative embodiments may be implemented. Other components in addition to or in place of the ones illustrated may be used. Some components may be optional.

In some illustrative embodiments, a heat pump system including a plurality of heat pump devices may be used along the main heat path of the imaging system 100. For example, a plurality of heat pump devices may be located at a plurality of positions along the main heat path to accelerate thermal energy transfer at each position, thereby increasing the heat dissipation capacity of the elongate member 102 and the heat dissipation capacity of the housing 106. The plurality of heat pump devices may create a plurality of selected temperature differences at the plurality of positions along the main heat path. Collectively or individually, the plurality of selected temperature differences at the respective position in the plurality of positions may be greater than the overall system temperature difference. Accordingly, the thermal energy, or heat, transferred at each of the plurality of positions is increased.

FIG. 3 is an illustration of a method for improving heat dissipation capacity, depicted in accordance with an illustrative embodiment. The method 300 illustrated in FIG. 3 may be used to improve the heat dissipation capacity along a medical instrument, such as the elongate member 102 between the tip 104 and the housing 106 of the imaging system 100 described in previous figures. The method 300 is illustrated as a set of operations or processes 302 and 304. Not all of the illustrated processes 302 and 304 may be performed in all embodiments of method 300. Additionally, one or more processes that are not expressly illustrated in FIG. 3 may be included before, after, in between, or as part of the processes 302 and 304. In some embodiments, one or more of the processes 302 and 304 may be optional and therefore omitted.

The method 300 may begin with a process 302 that includes generating thermal energy at a distal end of an elongate member. In process 302, the thermal energy may be generated by operating a powered component at or near the distal end. For example, without limitation, heat may be generated by operation of an illumination source, such as a light emitting diode at or near the distal end. In another example, heat may be generated by operation of an electronic component at or near the distal end.

At process 304, a heat pump device is activated. The heat pump may be thermally coupled between the elongate member and the housing.

At process 306, the thermal energy is transferred between the elongate member and the housing. Thus, the use of the heat pump may increase the heat dissipation capacity of the elongate member and the heat dissipation capacity of the housing, as compared to a similar system that omits the heat pump device. Accordingly, the heat pump device may allow more powerful components to be used at or near the distal tip, as compared to when the heat pump device is omitted. In one illustrative embodiment, the heat pump device may be a thermoelectric cooler. Depending on the implementation, the thermal energy may be transferred from the elongate member to the housing, from the housing to the elongate member, or both.

In greater detail, the heat pump device may control a temperature of the elongate member at a shaft side of the heat pump device. In some illustrative embodiments, the heat pump device may control the shaft side temperature at a level that is lower than an ambient temperature. Further, the heat pump device may control a temperature of the housing at a housing side of the heat pump device. In some illustrative embodiments, the heat pump device may control the housing side temperature at a value that is higher than a maximum contact temperature of the distal end 114.

FIG. 4 is an illustration of a method for improving heat dissipation capacity, depicted in accordance with an illustrative embodiment. The method 400 illustrated in FIG. 4 may be used to improve the heat dissipation capacity of an imaging system such as an endoscope. The method 400 is illustrated as a set of operations or processes 402-410. Not all of the illustrated processes 402-410 may be performed in all embodiments of method 400. Additionally, one or more processes that are not expressly illustrated in FIG. 4 may be included before, after, in between, or as part of the processes 402-410. In some embodiments, one or more of the processes 402-410 may be optional and therefore omitted.

The method may begin with a process 402 that includes inserting a distal end of an endoscope inside a patient anatomy. At process 404, an illumination source located at the distal end of the endoscope is activated. The illumination source may be, for example, a light emitting diode. Activating the light emitting diode may include, for example, supplying power to the light emitting diode. In this example, heat is generated at the distal end of the endoscope in response to activation of the light emitting diode.

At process 406, heat generated at the distal end of the endoscope is conveyed along a shaft of the endoscope. At process 408, the heat is transferred from the shaft to a housing of the endoscope through a heat pump device. The heat pump device may increase the shaft heat dissipation capacity and the housing dissipation capacity. In process 408, the housing is located outside of the patient's anatomy.

In process 408, the heat pump device maintains a shaft side temperature at a value below an ambient temperature of the ambient environment around the housing. Further, the heat pump device may be used to maintain the housing side temperature at a value above a maximum contact temperature for the distal end 114 of the endoscope. Accordingly, the heat pump device creates a temperature difference between the shaft and the housing that is greater than the overall system temperature difference between the distal end 114 and the ambient environment, thereby increasing the heat dissipation capacity of the shaft and the heat dissipation capacity of the housing. In other illustrative embodiments, the heat pump device may be used to maintain the housing side temperature at a value below the maximum contact temperature for the distal end 114 of the endoscope but above the ambient temperature.

At process 410, the heat is dissipated from the housing into an ambient environment around the housing. This type of dissipation may also be referred to as sinking the heat into the ambient environment.

Figure 5:
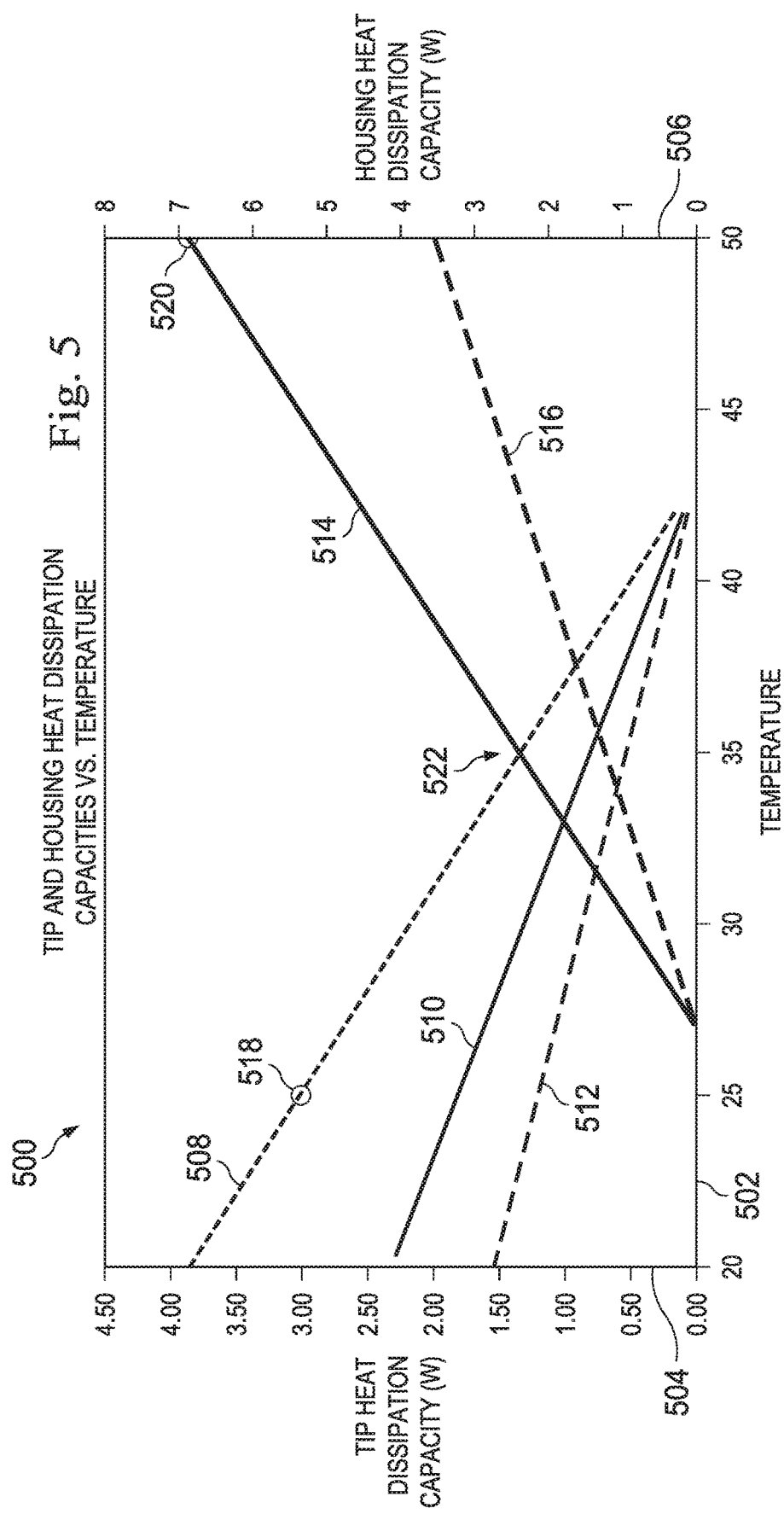
FIG. 5 is a graph of tip and housing heat dissipation capacities versus elongate member and housing temperatures in accordance with an illustrative embodiment.

FIG. 5 is a graph 500 of tip and housing heat dissipation capacities versus elongate member and housing temperatures, depicted in accordance with an illustrative embodiment. The graph 500 illustrates how using the heat pump device 108 of the imaging system 100 in FIG. 1 can increase the heat dissipation capacity of the elongate member 102 and thus the distal end 114 and also the housing heat dissipation capacity of the housing 106 in FIG. 1.

The graph 500 includes a temperature axis 502, a tip heat dissipation capacity axis 504, and a housing heat dissipation capacity axis 506. The temperature axis 502 identifies temperature values in degrees Celsius. The tip heat dissipation capacity axis 504 identifies heat dissipation capacity values for the tip 104 at the distal end 114 in Watts. The housing heat dissipation capacity axis 506 identifies heat dissipation capacity values for the housing 106 in Watts.

The graph 500 also includes a line 508, a line 510, a line 512, a line 514, and a line 516. In this illustrative example, the first line 508 represents the heat dissipation capacity of the elongate member 102 of the imaging system 100 when the elongate member 102 has a thermal resistance of about 6 degrees Celsius per Watt. The second line 510 represents the heat dissipation capacity of the elongate member 102 of the imaging system 100 when the elongate member 102 has a thermal resistance of about 10 degrees Celsius per Watt. The third line 512 represents the heat dissipation capacity of the elongate member 102 of the imaging system 100 when the elongate member 102 has a thermal resistance of about 15 degrees Celsius per Watt.

Further, the first housing line 514 represents the heat dissipation capacity of the housing 106 of the imaging system 100 when the housing is comprised of aluminum. The second housing line 516 represents the heat dissipation capacity of the housing 106 of the imaging system 100 when the housing is comprised of stainless steel.

In this illustrative embodiment, the housing 106 may have a length of about 120 millimeters and a thermal transmittance of about 30 Watts per meter-squared-Kelvin (W/m²K). The ambient temperature of the ambient environment 118 around the housing 106 may be set to about 27 degrees Celsius. Further, the maximum contact temperature for the distal end 114, and therefore the tip 104, may be about 42 degrees Celsius. Thus, the overall system temperature difference may be the difference between the maximum contact temperature and the ambient temperature, which is about 15 degrees Celsius.

Using the heat pump device 108 between the elongate member 102 and the housing 106, the temperature of the elongate member 102 is decoupled from the temperature of the housing 106 at heat pump device 108. For example, the heat pump device 108 may be used to keep the elongate member 102 at a lower temperature than the ambient temperature and to keep the housing 106 at a higher temperature than the maximum contact temperature for the distal end 114.

As illustrated by the point 518 along the line 510, when the housing 106 is made of aluminum and the elongate member has a thermal resistance of about 6 degrees Celsius per Watt, the heat pump device 108 may be used to maintain the shaft side temperature at about 25 degrees Celsius. Further, as indicated by the point 520 along the line 514, the heat pump device 108 may be used to maintain the housing side temperature at about 50 degrees Celsius. Thus, the temperature difference created between the elongate member 102 and the housing 106 may be about 25 degrees Celsius, which is greater than the overall system temperature difference.

By creating this larger temperature difference between the elongate member 102 and the housing 106, the heat pump device may increase the tip heat dissipation capacity to about 3 Watts and the housing dissipation capacity to about 7 Watts. If the heat pump device generates waste heat at a rate less than the 4-Watt difference between the housing and tip heat dissipation capacities, the heat pump device may be able to dissipate the heat from both the tip and the waste heat from the heat pump device.

As indicated by the intersection 522 of the first line 510 and the line 514, without the heat pump device 108, the elongate member 102 and the housing 106 would have a temperature of about 35 degrees Celsius at the joint between the elongate member 102 and the housing 106. Further, without the heat pump device 108, the tip dissipation capacity would only be about 1.33 Watts and the housing dissipation capacity would only be about 2.37 Watts.

Thus, the illustrative embodiments provide a method and apparatus for improving heat dissipation capacities along a medical instrument, such as an endoscope. Improving the tip and housing heat dissipation capacities allows components that generate a greater amount of heat to be used at or near the tip of endoscope. For example, higher-powered light emitting diodes may be used at the tip of the endoscope to provide better illumination without exceeding the maximum contact temperature of the tip or needing to redesign the housing or change the ambient temperature.

Further, using a thermoelectric cooler as the heat pump device may not add any undesired weight or bulk to the endoscope. Additionally, using a thermoelectric cooler may ensure that additional undesired acoustic or electrical noise is not produced during operation of the endoscope.

While certain exemplary embodiments of the invention have been described and shown in the accompanying drawings, it is to be understood that such embodiments are merely illustrative of and not restrictive on the broad invention. Additionally, it is to be understood that the embodiments of the invention are not limited to the specific constructions and arrangements shown and described, since various other modifications may occur to those ordinarily skilled in the art.

Further, in the detailed description of the embodiments of the invention, numerous specific details have been set forth in order to provide a thorough understanding of the disclosed embodiments. However, it will be obvious to one skilled in the art that the embodiments of this disclosure may be practiced without these specific details. In some instances, well known methods, procedures, and components have not been described in detail so as not to unnecessarily obscure aspects of the embodiments of the invention.

What is claimed is:

1. An apparatus comprising:
   an elongate member having a distal end and a proximal end;
   a housing coupled to the proximal end of the elongate member; and
   a heat pump device disposed between the proximal end of the elongate member and the housing, the heat pump device being disposed at least partially outside the housing and configured to transfer thermal energy between the elongate member and the housing, wherein the heat pump device has a maximum outer diameter that is greater than a maximum outer diameter of the elongate member.

2. The apparatus of claim 1, wherein the heat pump device comprises:
   a first side coupled to the proximal end of the elongate member; and
   a second side coupled to the housing.

3. The apparatus of claim 2, wherein the heat pump device controls a first temperature of the elongate member at the first side of the heat pump device such that the first temperature is lower than an ambient temperature around the housing.

4. The apparatus of claim 2, wherein the heat pump device controls a second temperature of the housing at the second side of the heat pump device such that the second temperature is higher than a maximum contact temperature of the distal end of the elongate member.

5. The apparatus of claim 2, wherein the heat pump device dissipates a waste heat generated by the heat pump device through the housing.

6. The apparatus of claim 2, wherein the heat pump device is configured to transfer thermal energy from the elongate member to the housing such that a proximal end temperature of the proximal end of the elongate member is less than a housing temperature of the housing.

7. The apparatus of claim 1, wherein the heat pump device includes a thermoelectric cooler.

8. The apparatus of claim 1 wherein the distal end of the elongate member includes a heat generating device that generates the thermal energy.

9. The apparatus of claim 1, wherein the heat pump device is configured to change a first heat dissipation capacity of the elongate member and to change a second heat dissipation capacity of the housing.

10. The apparatus of claim 9, wherein the heat pump device comprises:
    a first side coupled to the proximal end of the elongate member; and
    a second side coupled to the housing.

11. The apparatus of claim 10, wherein the heat pump device controls a first temperature of the elongate member at the first side of the heat pump device such that the first temperature is lower than an ambient temperature around the housing.

12. The apparatus of claim 10, wherein the heat pump device controls a second temperature of the housing at the second side of the heat pump device such that the second temperature is higher than a maximum contact temperature of the distal end of the elongate member.

13. The apparatus of claim 9, wherein the heat pump device causes a first temperature of the elongate member to be maintained at substantially a first value that is lower than an ambient temperature around the housing and causes a second temperature of the housing to be maintained at substantially a second value that is higher than a maximum contact temperature of the distal end of the elongate member.

14. The apparatus of claim 9, wherein the heat pump device provides dissipation of a waste heat generated by the heat pump device when a rate at which the waste heat is generated is less than a difference between the second heat dissipation capacity and the first heat dissipation capacity.

15. The apparatus of claim 9, wherein the heat pump device transfers heat from the elongate member to the housing such that a proximal end temperature of the proximal end of the elongate member is less than a housing temperature of the housing.

16. The apparatus of claim 9, wherein the heat pump device includes a thermoelectric cooler.

17. The apparatus of claim 9, wherein the distal end of the elongate member includes a heat generating device that changes the first heat dissipation capacity of the elongate member and changes the second heat dissipation capacity of the housing.

18. An apparatus comprising:
    an elongate member having a distal end and a proximal end;
    a housing located near the proximal end of the elongate member; and
    a plurality of heat pump devices each located at a respective one of a plurality of positions along a heat path formed between the distal end of the elongate member and the housing, wherein the plurality of heat pump devices are disposed at least partially outside the housing and configured to transfer thermal energy between the elongate member and the housing,
    wherein at least one heat pump device of the plurality of heat pump devices is disposed between the proximal end of the elongate member and the housing and has a maximum outer diameter that is greater than a maximum outer diameter of the elongate member.

19. The apparatus of claim 18, wherein collectively the plurality of heat pump devices create an internal temperature difference and wherein the internal temperature difference is greater than an overall system temperature difference.

20. The apparatus of claim 19, wherein the overall system temperature difference is bounded by a maximum contact temperature of the distal end of the elongate member and an ambient temperature of an environment around the housing.

\* \* \* \* \*